United States Patent
Hendriksen (10) Patent No.: US 11,666,845 B2
(45) Date of Patent: Jun. 6, 2023

(54) AIR PURIFICATION DEVICE

(71) Applicant: Respired Limited, London (GB)

(72) Inventor: Henrik Victor Hendriksen, Aalborg (DK)

(73) Assignee: RESPIRED LIMITED, London (GB)

( * ) Notice: Subject to any disclaimer, the term of this patent is extended or adjusted under 35 U.S.C. 154(b) by 447 days.

(21) Appl. No.: 16/931,594

(22) Filed: Jul. 17, 2020

(65) Prior Publication Data

US 2022/0016558 A1 Jan. 20, 2022

(51) Int. Cl.
 *B01D 46/00* (2022.01)
 *B01D 46/52* (2006.01)
 (Continued)

(52) U.S. Cl.
 CPC .......... *B01D 46/0028* (2013.01); *A61L 9/014* (2013.01); *A61L 9/20* (2013.01); *B01D 46/0006* (2013.01); *B01D 46/0008* (2013.01); *B01D 46/0038* (2013.01); *B01D 46/0043* (2013.01); *B01D 46/0093* (2013.01);
 (Continued)

(58) Field of Classification Search
 CPC ........ A61L 9/20; A61L 9/014; A61L 2209/12; A61L 2209/14; A61L 2209/22; B01D 46/0028; B01D 46/2411; B01D 46/0006; B01D 46/0008; B01D 46/0038; B01D 46/0043; B01D 46/0093; B01D 46/521; B01D 46/522; B01D 46/442; B01D 46/46;
 (Continued)

(56) References Cited

U.S. PATENT DOCUMENTS 5,399,319 A * 3/1995 Schoenberger .... B01D 46/0028
                                                         55/385.2
5,997,619 A   12/1999 Knuth et al.
               (Continued)

FOREIGN PATENT DOCUMENTS

CN         105498378 A  *  4/2016
CN         205227572 U     5/2016
               (Continued)

OTHER PUBLICATIONS

Machine translation of WO2020214068 (Year: 2020).*
Machine translation of CN105498378 (Year: 2016).*
Machine translation of CN108019840 (Year: 2018).*

*Primary Examiner* — Robert Clemente
(74) *Attorney, Agent, or Firm* — Elevated IP, LLC (57) ABSTRACT

A purification device for disinfecting and filtering intake air is disclosed. The purification device comprises a housing provided with a number of inlet perforations for allowing the intake air to enter the housing and a number of air outlet perforations for allowing air purified by the purification device to leave the housing. The purification device moreover comprises a fan arranged inside the housing to suck the intake air into the housing and blow the purified air out of the housing. The purification device further comprises an ultraviolet radiation lamp arranged inside the housing to irradiate the intake air. The purification device also comprises a high-efficiency particulate air (HEPA) filter arranged to filter the intake air before the intake air leaves the housing as purified air. The filter comprises a plurality of pleats arranged in such a manner that the angle between adjacent pleats is 30 degrees or less.

24 Claims, 6 Drawing Sheets

(51) Int. Cl.
*B01D 46/44* (2006.01)
*B01D 46/46* (2006.01)
*A61L 9/20* (2006.01)
*A61L 9/014* (2006.01)

(52) U.S. Cl.
CPC ............ *B01D 46/442* (2013.01); *B01D 46/46* (2013.01); *B01D 46/522* (2013.01); *A61L 2209/12* (2013.01); *A61L 2209/14* (2013.01); *A61L 2209/22* (2013.01); *B01D 2267/40* (2013.01); *B01D 2273/26* (2013.01); *B01D 2273/30* (2013.01); *B01D 2279/65* (2013.01)

(58) Field of Classification Search
CPC ............ B01D 2267/40; B01D 2273/26; B01D 2273/30; B01D 2279/65
See application file for complete search history.

(56) References Cited

U.S. PATENT DOCUMENTS

| | | | |
|---|---|---|---|
| 2004/0112221 A1 | 6/2004 | Tillman | |
| 2004/0166037 A1 | 8/2004 | Youdell et al. | |
| 2004/0184949 A1 | 9/2004 | McEllen | |
| 2006/0201119 A1 | 9/2006 | Song | |
| 2010/0095844 A1* | 4/2010 | Gilleland | A61L 9/20 96/16 |
| 2013/0239803 A1 | 9/2013 | Palmer | |
| 2022/0373203 A1* | 11/2022 | Zhou | F24H 3/002 |

FOREIGN PATENT DOCUMENTS

| | | | | |
|---|---|---|---|---|
| CN | 205948667 U | | 2/2017 | |
| CN | 207162759 U | | 3/2018 | |
| CN | 108019840 A | * | 5/2018 | |
| CN | 209386448 U | | 9/2019 | |
| WO | 03068273 A1 | | 8/2003 | |
| WO | WO-2020214068 A1 | * | 10/2020 | ............ B01D 46/52 |

* cited by examiner

AIR PURIFICATION DEVICE

FIELD OF INVENTION

The present invention relates to an air purification device. The present invention more particularly relates to a portable air purification device.

BACKGROUND

Population growth compounded with rapid urbanization has amplified the potential for bacteria and viruses to spread quickly. Accordingly, there is an increasing need for purification and disinfection of air in order to eliminate the risk of infecting vulnerable hospitalized people and nursing home residents. The Coronavirus Disease COVID-19 has brought the risk of infecting vulnerable older or hospitalized people as well as nursing home residents with various diseases into focus.

Thus, there is a need for an air purification device that can reduce the risk of infecting vulnerable people with viruses such as the Coronavirus causing the Coronavirus Disease COVID-19.

Most viruses vary in diameter from 20 nm to 400 nm. Accordingly, even though many prior art air purification devices comprise an efficiency standard of air filter such as a high-efficiency particulate air (HEPA) filter, these purification devices cannot effectively filter viruses due to the small size of viruses. Accordingly, the prior art air purification devices cannot be used to protect from airborne or aerosolized pathogens.

Filters meeting the HEPA standard must remove from the air that passes through the filter at least 99.95% (European Standard) or 99.97% (ASME, U.S. DOE), respectively, of particles whose diameter is equal to 0.3 µm.

It is an object of the present invention to provide an air purification device that can efficiently purify virus containing air and thus reduce the risk of infecting vulnerable people with viruses that cause infectious diseases.

SUMMARY

The object of the present invention can be achieved by purification units and methods disclosed herein.

A purification device according to the invention is a purification device for disinfecting and filtering intake air, wherein the purification device comprises:
- a housing provided with a number of inlet perforations for allowing the intake air to enter the housing and a number of air outlet perforations for allowing air purified by the purification device to leave the housing;
- a fan arranged inside the housing to suck the intake air into the housing and blow the purified air out of the housing;
- an ultraviolet radiation lamp arranged inside the housing to irradiate the intake air;
- a high-efficiency particulate air (HEPA) filter surrounding the ultraviolet radiation lamp and being arranged to filter the intake air before the intake air leaves the housing as purified air, wherein the filter comprises a plurality of pleats arranged in such a manner that the angle between adjacent pleats is 30 degrees or less.

Due to the small acute angle θ, the retention capability of the filter can be increased. Therefore, the purification device provides a more efficient purification of virus containing air. Accordingly, by using the purification device to purify the air that vulnerable people are exposed to (e.g. in a hospital room or a room in a nursing home) it is possible to reduce the risk of infecting vulnerable people with viruses that cause infectious diseases.

In one embodiment, the angle between adjacent pleats is 28 degrees. In one embodiment, the angle between adjacent pleats is 26 degrees. In one embodiment, the angle between adjacent pleats is 24 degrees. In one embodiment, the angle between adjacent pleats is 22 degrees. In one embodiment, the angle between adjacent pleats is 20 degrees. In one embodiment, the angle between adjacent pleats is 18 degrees. In one embodiment, the angle between adjacent pleats is 16 degrees. In one embodiment, the angle between adjacent pleats is 15 degrees. In one embodiment, the angle between adjacent pleats is 14 degrees. In one embodiment, the angle between adjacent pleats is 12 degrees. In one embodiment, the angle between adjacent pleats is 10 degrees. In one embodiment, the angle between adjacent pleats is 8 degrees or less.

The number of pleats is inversely related to the angle between adjacent pleats. Accordingly, it is possible to achieve a small angle between adjacent pleats by applying a large number of pleats.

Moreover, the total filter area is proportional to the number of pleats. Accordingly, it is possible to increase the total filter area by increasing the number of pleats. It is an advantage to have a large filter area because the filtering capacity (the maximum flow velocity) is proportional to the filter area.

The small angle between adjacent pleats makes it possible to make the virus stick to inside surfaces of the HEPA filter. Since the filter surrounds the ultraviolet radiation lamp, there is plenty of time to eliminate the virus by emitting ultraviolet radiation. Accordingly, the purification unit has a unique ability to maintain virus particles inside the space surrounded by the filter and irradiate the virus particles with ultraviolet radiation that destroys the virus particles.

Since the filter does not allow any virus particles to pass through the filter and since any virus particles present at the inside surface of the filter are killed by the ultraviolet radiation from the ultraviolet radiation lamp, the filter contains no virus particles when the filter has to be replace (during maintenance). Accordingly, it is not required for service personnel to wear a hazmat suit or biohazard suit when replacing the filter. Moreover, service personnel can remove the filter without risking infection and the filter will not contain any virus particles when the purification device is turned off. Accordingly, it is safe to move the purification device from one room to another.

In one embodiment, the distance from the UV lamp to the inside part of the HEPA filer is less than 20 cm.

In one embodiment, the distance from the UV lamp to the inside part of the HEPA filer is less than 18 cm.

In one embodiment, the distance from the UV lamp to the inside part of the HEPA filer is less than 16 cm.

In one embodiment, the distance from the UV lamp to the inside part of the HEPA filer is less than 14 cm.

In one embodiment, the housing is cylindrical.

In one embodiment, the housing is box-shaped.

In one embodiment, the HEPA filter area is 2 square meters or more. In one embodiment, the HEPA filter area is 3 square meters or more. In one embodiment, the HEPA filter area is 4 square meters or more.

In one embodiment, the lowest position of the UV lamp is the distal portion of the UV lamp, wherein an air gap is provided between the bottom plate of the housing and the distal portion of the UV lamp.

Hereby, shadow areas (non-irradiated intake air leaving the housing) can be avoided. Moreover, particles that fall down to the bottom plate of the housing will be exposed to UV radiation from the UV lamp. Accordingly, particles on the bottom plate will be destroyed by the UV radiation.

In one embodiment, the light irradiation portion of the UV lamp extends vertically.

In one embodiment, the housing comprises a bottom portion and a top portion configured to be detachably attached to the bottom portion. Hereby, access to the structures inside the housing is eased. This is an advantage during maintenance and replacements.

In one embodiment, the fan is arranged in the top portion and the light irradiation portion of the UV lamp is arranged in the bottom portion. Hereby, it is possible to introduce intake air into the top portion of the housing and blow the intake air into the bottom portion of the housing and carry out a UV irradiation treatment of the air that is blown into the bottom portion of the housing.

In one embodiment, the inlet perforations are provided in the top portion, whereas the outlet perforations are provided in the bottom portion. Hereby, it is possible to guide the intake air into the top portion of the housing through the inlet perforations and blow the purified air out of the bottom portion of the housing through outlet perforations. Accordingly, the air flow pattern can be controlled in a simple and reliable manner.

In one embodiment, the fan has a horizontally orientated intake portion and a vertical output portion so that air pressurized by the fan leaves the fan in a downwardly vertical direction. Since the intake air enters the purification device in the top portion of the purification device, the intake air will not suck particles from floor level into the purification device. The purified air will leave the purification device in a lower level than the level at which intake air enters the purification device.

Since the intake air enters the purification device in the top portion of the purification device, which is more than 200 mm above floor level, the purification device meets the requirements for being used in Scandinavian hospitals, in which the floor zone and the zone extending 200 mm above the floor is considered to be contaminated.

In one embodiment, the intake air enters the purification device in the top portion of the purification device, which is more than 400 mm above floor level.

In one embodiment, the intake air enters the purification device in the top portion of the purification device, which is in the range of 500-700 mm above floor level.

In one embodiment, the height of the purification device is 60-100 cm.

In one embodiment, the height of the purification device is 70-90 cm.

In one embodiment, the height of the purification device is 75-85 cm such as 80 cm.

In one embodiment, the purification device is cylindrical and has a diameter in the range of 30-55 cm.

In one embodiment, the purification device is cylindrical and has a diameter in the range of 35-50 cm.

In one embodiment, the purification device is cylindrical and has a diameter in the range of 40-45 cm such as 42 cm.

In one embodiment, the fan is configured to deliver a flow up to 600 $m^3$/hour.

In one embodiment, the fan is configured to deliver a flow up to 560 $m^3$/hour.

In one embodiment, an additional layer is arranged at the outside of the filter.

In one embodiment, the additional layer comprises activated carbon.

It may be advantageous that an additional layer is sandwiched between the housing and the filter, wherein the additional layer comprises activated carbon. Hereby, the activated carbon can remove unwanted odors by acting as an adsorbent which will trap the odor inside the activated carbon and retain it. Moreover, the additional layer can prevent UV light from escaping to the surroundings.

In one embodiment, the top portion comprises a coarse filter slidably arranged in one or more filter tracks extending axially near the rim of the top portion. Hereby, replacement of the coarse filter is eased.

In one embodiment, the top portion comprises two, three or four separated filter segments constituting a coarse filter, wherein the filter segments are slidably arranged in filter tracks extending axially near the rim of the top portion.

In one embodiment, the top portion comprises four coarse filter segments that are slidably arranged in filter tracks extending axially near the rim of the top portion.

In one embodiment, the purification device comprises a particle sensor arranged to detect the level of particles in the air.

In one embodiment, the particle sensor is arranged inside the housing. Hereby, the particle sensor can detect the level of particles in the intake air entering the housing.

In one embodiment, the particle sensor is arranged inside the top portion of the housing. Hereby, the particle sensor can detect the level of particles in the intake air entering the top portion of the housing.

In one embodiment, the particle sensor is arranged inside the bottom portion of the housing. Hereby, the particle sensor can detect the level of particles in the intake air entering the bottom portion of the housing.

In one embodiment, the purification device comprises a smoke alarm. Accordingly, the purification device can alert the people in the same room as the purification device in case of a fire.

In one embodiment, the smoke alarm is arranged inside the housing. Hereby, the smoke alarm can detect the level of smoke in the intake air entering the housing.

In one embodiment, the smoke alarm is arranged inside the top portion of the housing. Hereby, the smoke alarm can detect the level of smoke in the intake air entering the top portion of the housing.

In one embodiment, the smoke alarm is arranged inside the bottom portion of the housing. Hereby, the smoke alarm can detect the level of smoke in the intake air entering the bottom portion of the housing.

In one embodiment, the purification device comprises a control unit configured to control the speed of the fan depending on the detected level of particles in the air.

In one embodiment, the control unit is configured to control the speed of the fan depending on measurements made by the smoke alarm.

In one embodiment, the control unit is configured to turn on the fan if the particle content of the intake air exceeds a predefined level.

In one embodiment, the control unit is configured to turn on the UV lamp if the particle content of the intake air exceeds a predefined level.

In one embodiment, the control unit is configured to turn on the fan and the UV lamp if the particle content of the intake air exceeds a predefined level.

In one embodiment, the control unit is configured to regulate the speed of the fan depending on the detected level of particle content (detected by the particle sensor).

In one embodiment, the control unit is configured to adjust the speed of the fan to one of two or more predefined non-zero levels.

In one embodiment, the control unit is configured to adjust the speed of the fan to one of three or more predefined non-zero levels.

In one embodiment, the control unit is configured to adjust the speed of the fan in an ungraduated manner on the basis of the detected level of particle content. This may be done by fitting the fan with a permanent magnet motor and a frequency converter. This will furthermore allow the provision of the lowest possible energy consumption.

In one embodiment, the predefined particle content level is a default quantity. In another embodiment, however, the predefined particle content level can be adjusted by using a control unit of the purification device.

A method according to the invention is a method for disinfecting and filtering intake air, wherein the method comprises the following steps:

sucking intake air into a housing by means of a fan arranged inside the housing, wherein the intake air enters the housing through a number of inlet perforations provided in the housing;

blowing purified air by means of the fan out from the housing through a number of air outlet perforations provided in the housing;

irradiating the intake air by means of an ultraviolet radiation lamp arranged inside the housing;

filtering the intake air by means of a HEPA filter before the intake air leaves the housing as purified air, wherein the method comprises the step of applying a filter that comprises a plurality of pleats arranged in such a manner that the angle between adjacent pleats is 30 degrees or less.

Accordingly, the method provides a way of purifying the air that vulnerable people are exposed to (e.g. in a hospital room or a room in a nursing home) in an improved manner. Accordingly, the method makes it possible to reduce the risk of infecting vulnerable people with viruses that cause infectious diseases.

In one embodiment, the angle between adjacent pleats is 28 degrees. In one embodiment, the angle between adjacent pleats is 26 degrees. In one embodiment, the angle between adjacent pleats is 24 degrees. In one embodiment, the angle between adjacent pleats is 22 degrees. In one embodiment, the angle between adjacent pleats is 20 degrees. In one embodiment, the angle between adjacent pleats is 18 degrees. In one embodiment, the angle between adjacent pleats is 16 degrees. In one embodiment, the angle between adjacent pleats is 15 degrees. In one embodiment, the angle between adjacent pleats is 14 degrees. In one embodiment, the angle between adjacent pleats is 12 degrees. In one embodiment, the angle between adjacent pleats is 10 degrees. In one embodiment, the angle between adjacent pleats is 8 degrees or less.

The number of pleats is inversely related to the angle between adjacent pleats. Accordingly, it is possible to achieve a low angle between adjacent pleats by applying more pleats.

Moreover, since the total filter area is proportional to the number of pleats, it is possible to increase the total filter area by increasing the number of pleats.

In one embodiment, the irradiation is carried out by using a UV lamp, wherein the lowest position of the UV lamp is the distal portion of the UV lamp, wherein an air gap is provided between the bottom plate of the housing and the distal portion of the UV lamp.

Accordingly, shadow areas (non-irradiated intake air leaving the housing) can be avoided. Moreover, particles that fall down to the bottom plate of the housing will be exposed to UV radiation from the UV lamp.

In one embodiment, the light irradiation is carried out by using a UV lamp that extends vertically.

In one embodiment, the method applies a housing that comprises a bottom portion and a top portion configured to be detachably attached to the bottom portion.

In one embodiment, the method comprises the step of applying a fan that is arranged in the top portion, wherein the light irradiation portion of the UV lamp is arranged in the bottom portion.

In one embodiment, the method is carried out by using inlet perforations that are provided in the top portion of the housing and outlet perforations that are provided in the bottom portion of the housing.

In one embodiment, the method comprises the step of applying a fan that has a horizontally orientated intake portion and a vertical output portion so that air pressurized by the fan leaves the fan in a downwardly vertical direction.

In one embodiment, the method comprises the step of applying an additional layer arranged at the outside of the filter.

In one embodiment, the method comprises the step of applying an additional layer that comprises activated carbon.

In one embodiment, the method comprises the step of applying an additional layer that is sandwiched between the housing and the filter, wherein the additional layer comprises activated carbon.

Hereby, the activated carbon can remove unwanted odors by acting as an adsorbent which will trap the odor inside the activated carbon and retain it. Moreover, the additional layer can prevent UV light from escaping to the surroundings.

In one embodiment, the method comprises the step of applying a coarse filter to filter the intake air before the intake air is sucked into the fan.

In one embodiment, the method comprises the step of applying a particle sensor arranged to detect the level of particles in the air.

In one embodiment, the method comprises the step of applying a particle sensor arranged inside the housing. Hereby, the particle sensor can detect the level of particles in the intake air entering the housing.

In one embodiment, the method comprises the step of applying a particle sensor arranged inside the top portion of the housing. Hereby, the particle sensor can detect the level of particles in the intake air entering the top portion of the housing.

In one embodiment, the method comprises the step of applying a particle sensor arranged inside the bottom portion of the housing. Hereby, the particle sensor can detect the level of particles in the intake air entering the bottom portion of the housing.

The method comprises the step of applying a smoke alarm to detect the smoke content in the air.

The method comprises the step of applying a smoke alarm that is arranged inside the housing. Hereby, the smoke alarm can detect the level of smoke in the intake air entering the housing.

In one embodiment, the smoke alarm is arranged inside the top portion of the housing. Hereby, the smoke alarm can detect the level of smoke in the intake air entering the top portion of the housing.

The method comprises the step of applying a smoke alarm arranged inside the bottom portion of the housing. Hereby, the smoke alarm can detect the level of smoke in the intake air entering the bottom portion of the housing.

In one embodiment, the method comprises the step of controlling the speed of the fan depending on the detected level of particles in the air.

In one embodiment, the method comprises the step of applying a control unit that is configured to control the speed of the fan depending on measurements made by the smoke alarm.

In one embodiment, the method comprises the step of applying a control unit that is configured to turn on the fan if the particle content of the intake air exceeds a predefined level.

In one embodiment, the method comprises the step of applying a control unit that is configured to turn on the UV lamp if the particle content of the intake air exceeds a predefined level.

In one embodiment, the method comprises the step of applying a control unit that is configured to turn on the fan and the UV lamp if the particle content of the intake air exceeds a predefined level.

In one embodiment, the method comprises the step of applying a control unit that is configured to regulate the speed of the fan depending on the detected level of particle content (detected by the particle sensor).

In one embodiment, the control unit is configured to adjust the speed of the fan to one of two or more predefined non-zero levels.

In one embodiment, the method comprises the step of applying a control unit that is configured to adjust the speed of the fan to one of three or more predefined non-zero levels.

In one embodiment, the method comprises the step of applying a control unit that is configured to adjust the speed of the fan in an ungraduated manner on the basis of the detected level of particle content. This may be done by fitting the fan with a permanent magnet motor and a frequency converter. This will furthermore allow the provision of the lowest possible energy consumption.

In one embodiment, the predefined particle content level is a default quantity. In another embodiment, however, the predefined particle content level can be adjusted by using a control unit of the purification device.

DESCRIPTION OF THE DRAWINGS

The invention will become more fully understood from the detailed description given below. The accompanying drawings are given by way of illustration only, and thus, they are not limitative of the present invention. In the accompanying drawings.

DETAILED DESCRIPTION

Figure 1:
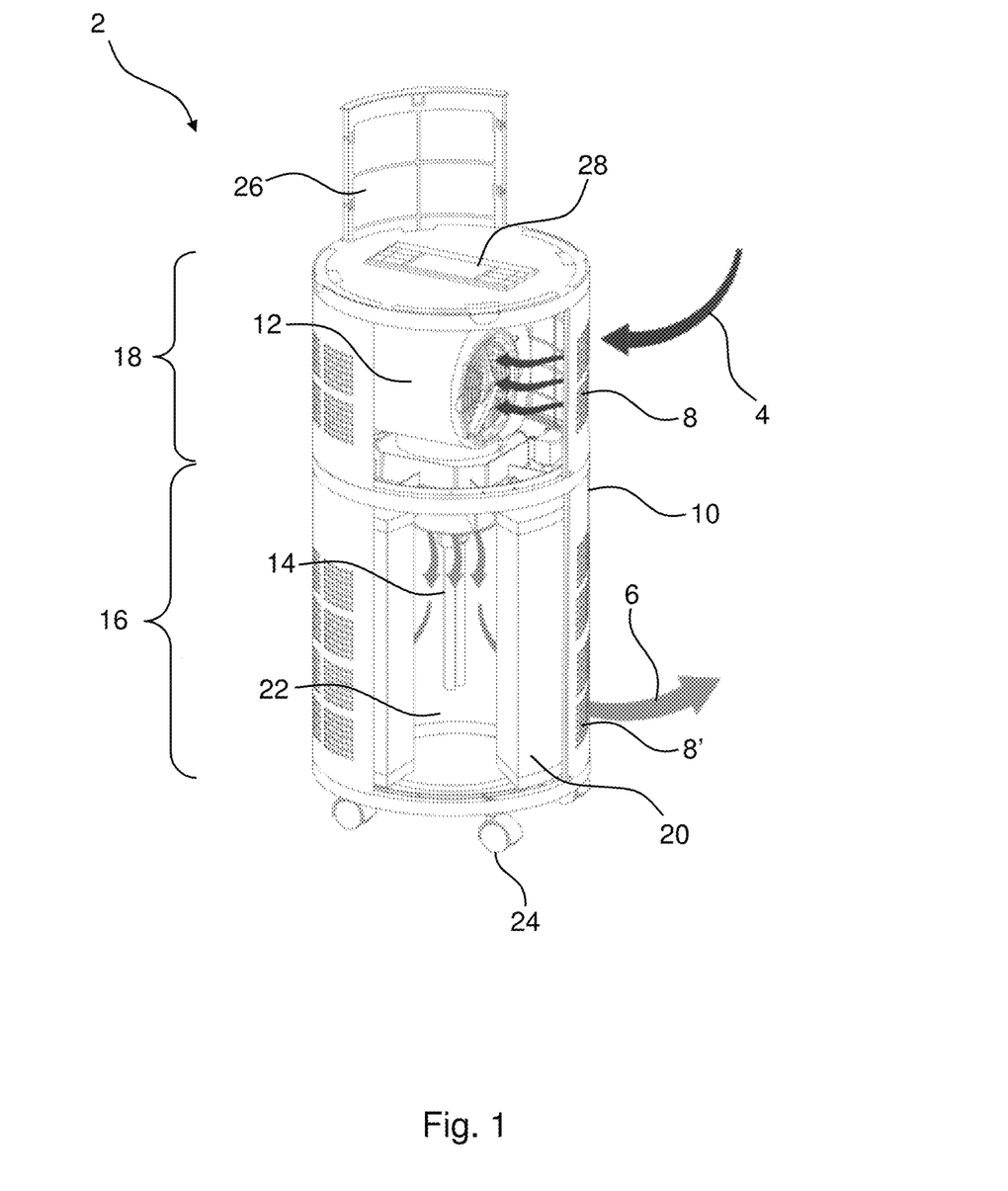
FIG. 1 shows a perspective side view of an air purification device according to the invention.

Referring now in detail to the drawings for the purpose of illustrating preferred embodiments of the present invention, an air purification device 2 of the present invention is illustrated in FIG. 1.

FIG. 1 is a perspective side view of an air purification device 2 according to the invention. The air purification device 2 comprises a housing 10 having a bottom portion 16 and a top portion 18 configured to be detachably attached to the bottom portion 16.

The bottom portion 16 is equipped with wheels 24 for improving the mobility of the air purification device 2.

The top portion 18 is cylindrical and comprises a panel 28 provided on the top of the top portion 18. In one embodiment, both the top portion 18 and the bottom portion 16 comprise a display and one or more buttons.

The top portion 18 comprises a coarse filter 26 separated into four filter segments that are slidably arranged in filter tracks extending axially near the rim of the top portion 18. A plurality of air inlet perforations 8 are provided in the cylindrical outer surface of the top portion 18. The coarse filter 26 is adapted to prevent objects larger than a predefined size (e.g. 5 or 20 µm) to enter the inner space of the top portion 18.

An electrically driven fan 12 is arranged inside the inner space of the top portion 18. The fan 12 is an axial fan designed to cause intake air 4 to flow through the fan 12 in an axial direction, parallel to the shaft about which the blades of the fan 12 rotate. The fan 12 has a horizontally orientated intake portion and a vertical output portion so that air pressurized by the fan 12 leaves the fan 12 in a downwardly vertical direction.

The bottom portion 16 comprises an inner space 22 defined by an enclosing cylindrical high-efficiency particulate air (HEPA) filter. An ultraviolet radiation lamp 14 is centrally arranged in the inner space 22. In a preferred embodiment, the ultraviolet radiation lamp 14 is a germicidal lamp (an ultraviolet C lamp). This may be an advantage since ultraviolet C light (wherein the wavelength is in the range of 100 to 280 nm) is capable of destroying and thus inactivating bacteria, viruses, and protozoa.

The UV C lamp 14 is arranged to irradiate the intake air 4 flowing into the inner space 22 of the bottom portion 16. Accordingly, the UV C lamp 14 is capable of disinfecting the intake air 4 flowing into the inner space 22 of the bottom portion 16.

The purification device is configured to receive intake air 4 through air inlet perforations 8 and allow the intake air 4 to flow through the filter 20 and leave the bottom portion 16 through air outlet perforations 8' provided in the housing 10. In the top portion 18, four coarse filter segments 26 are slidably arranged in filter tracks extending axially near the rim of the top portion.

Figure 2:
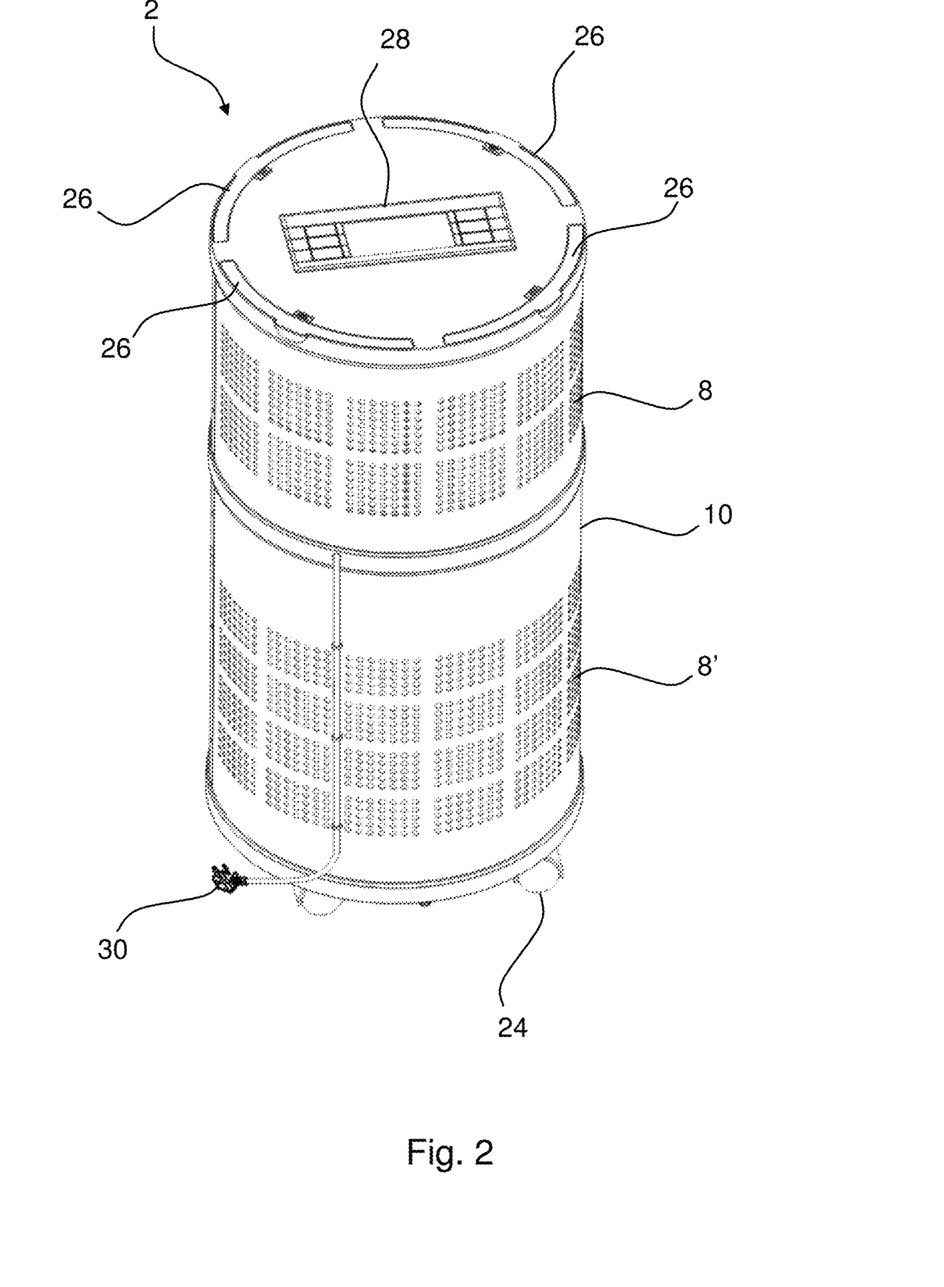
FIG. 2 shows a perspective top view of the purification device shown in FIG. 1.

FIG. 2 illustrates a perspective top view of the purification device 2 shown in FIG. 1. It can be seen that the purification device 2 comprises an electrical plug 30 for electrically connecting the purification device 2 to the main. Hereby, the fan inside the housing 10 of the purification device 2 can be powered. It can be seen that the top portion is provided with a plurality of air inlet perforations 8. The bottom portion is provided with a plurality of air outlet perforations 8'.

Figure 3A:
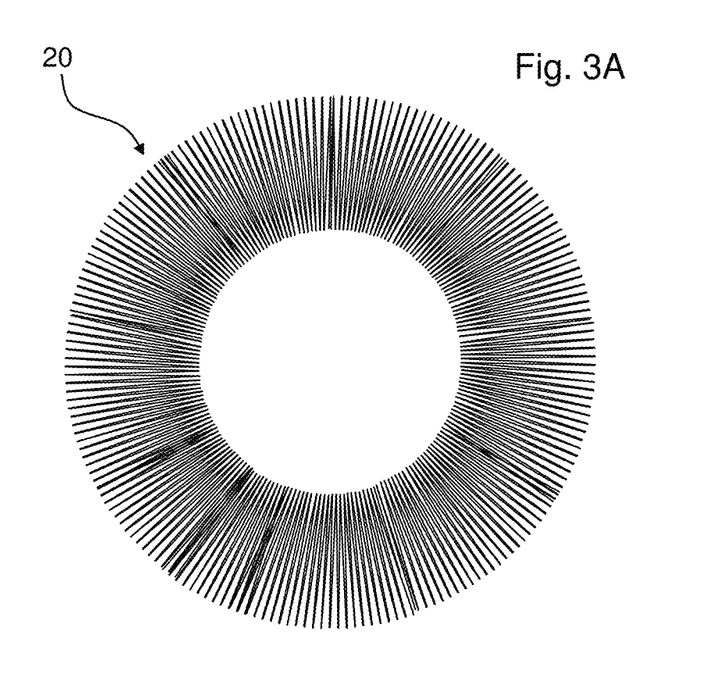
FIG. 3A shows a schematic top view of a filter according to the invention.

FIG. 3A illustrates a schematic top view of a filter 20 according to the invention. The filter 20 comprises a plurality of pleats.

Figure 3B:
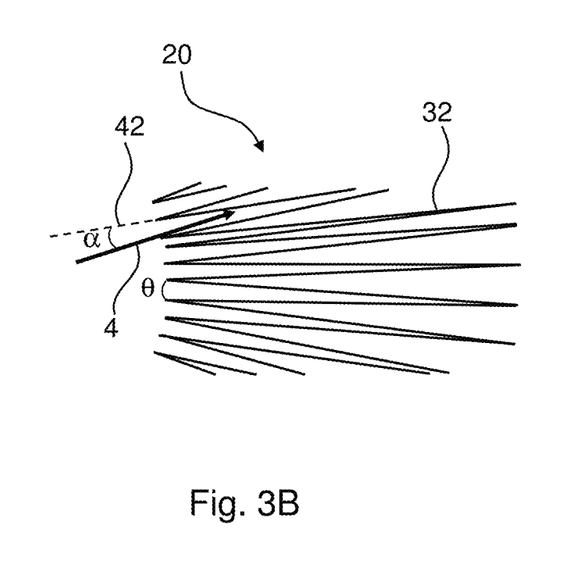
FIG. 3B shows a close-up view of the filter shown in FIG. 3A.
Figure 3C:
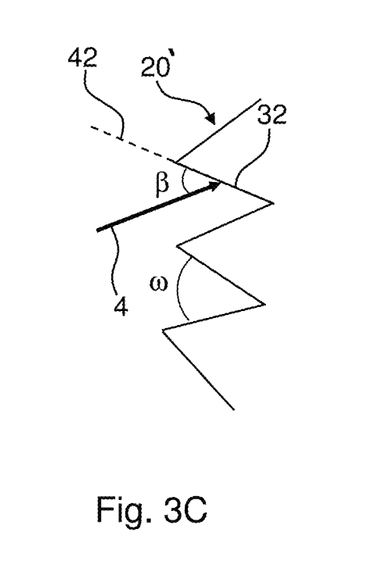
FIG. 3C shows a prior art filter.

FIG. 3B illustrates a close-up view of the filter 20 shown in FIG. 3A, and FIG. 3C illustrates a prior art filter 20'. It can be seen that the angle α between the air flow direction 42 and the side portion of the adjacent pleat 32 of the filter 20 shown in FIG. 3B is smaller than the angle β between the air flow direction 42 and the side portion of the adjacent pleat 32 of the prior art filter 20' shown in FIG. 3C. Moreover, it can be seen that the angle θ between adjacent pleats 32 of the filter 20 in the purification device 2 according to the invention is smaller than the angle ω between adjacent pleats 32 of the prior art filter 20' shown in FIG. 3C.

Due to the small acute angle θ, the retention capability of the filter 20 is increased by having an increased number of pleats 32 compared to the prior art filter shown in FIG. 3C.

In one embodiment, the angle θ is 30 degrees or less. In one embodiment, the angle θ is 28 degrees or less. In one embodiment, the angle θ is 26 degrees or less. In one embodiment, the angle θ is 24 degrees or less. In one embodiment, the angle θ is 22 degrees or less. In one embodiment, the angle θ is 20 degrees or less. In one embodiment, the angle θ is 18 degrees or less. In one embodiment, the angle θ is 16 degrees or less. In one embodiment, the angle θ is 14 degrees or less. In one embodiment, the angle θ is 12 degrees or less. In one embodiment, the angle θ is 10 degrees or less. In one embodiment, the angle θ is 8 degrees or less. The number of pleats 32 is inversely related to the angle θ. Accordingly, it is possible to achieve a low angle θ by applying more pleats 32.

Moreover, the total filter area is proportional to the number of pleats 32. Accordingly, it is possible to increase the total filter area by increasing the number of pleats 32.

Figure 4:
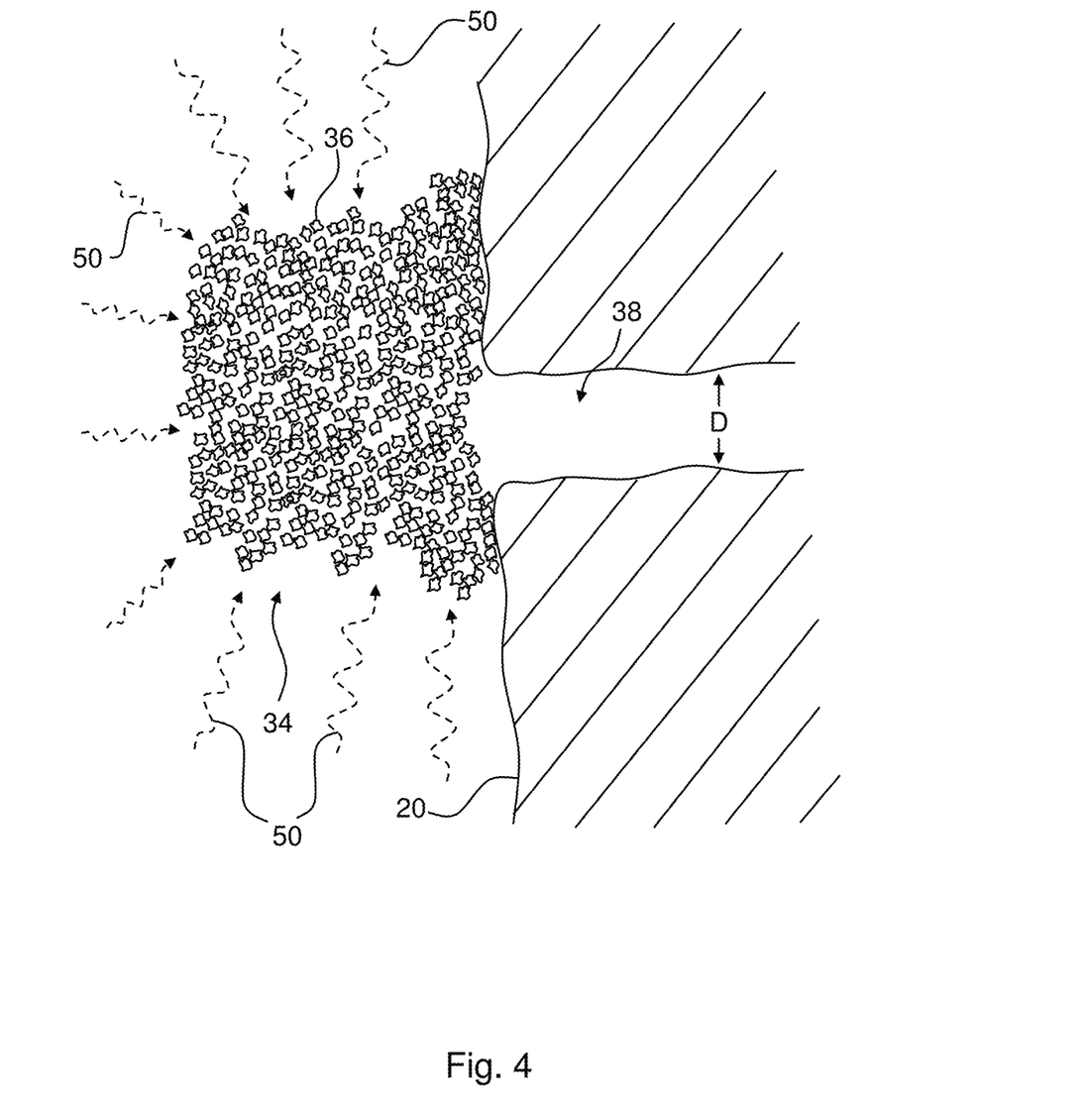
FIG. 4 shows a blown up (close-up) cross-sectional view of a portion of the inner space surrounded by a filter of a purification device according to the invention.
Figure 5:
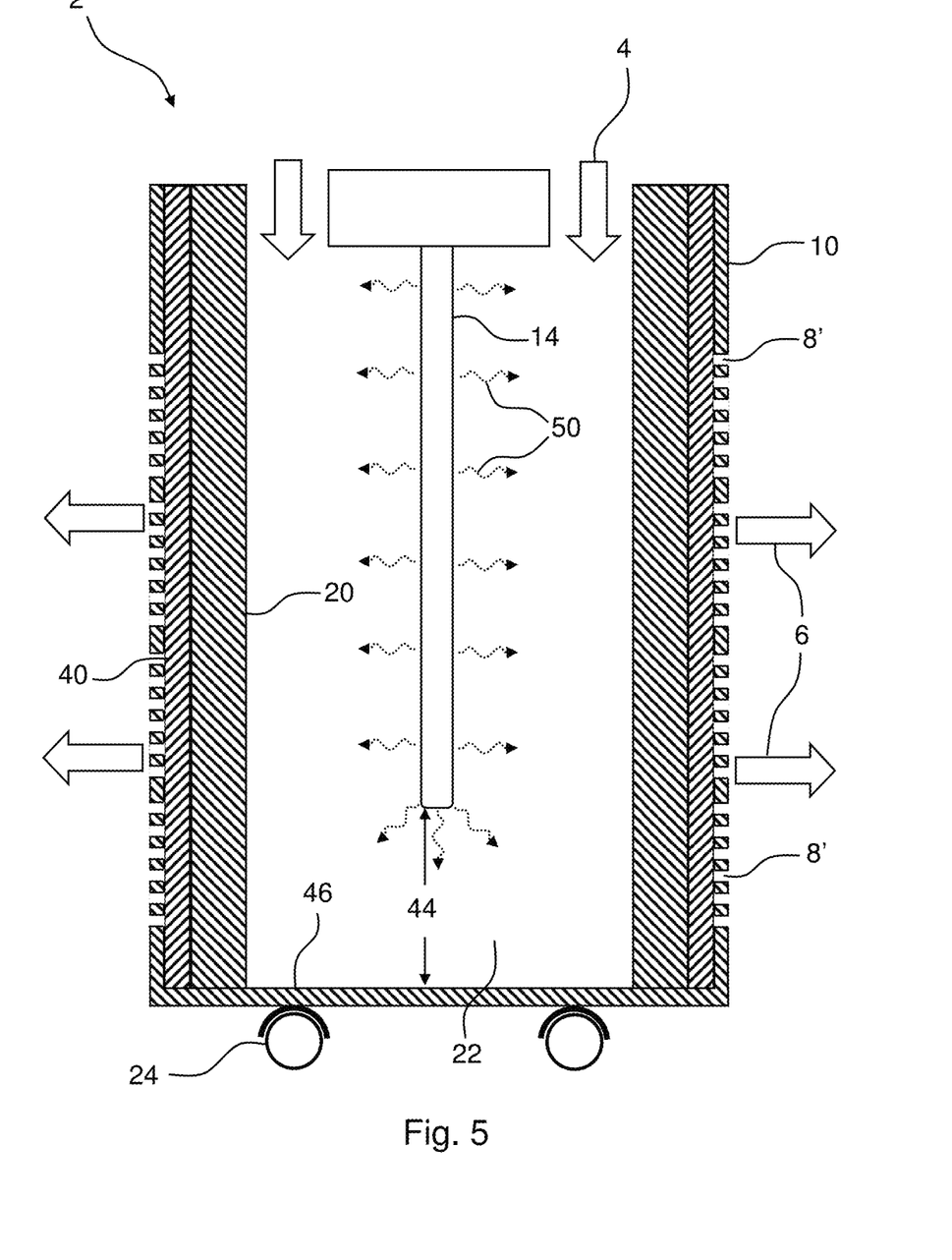
FIG. 5 shows a cross-sectional view of the bottom portion of a purification device according to the invention.
Figure 6:
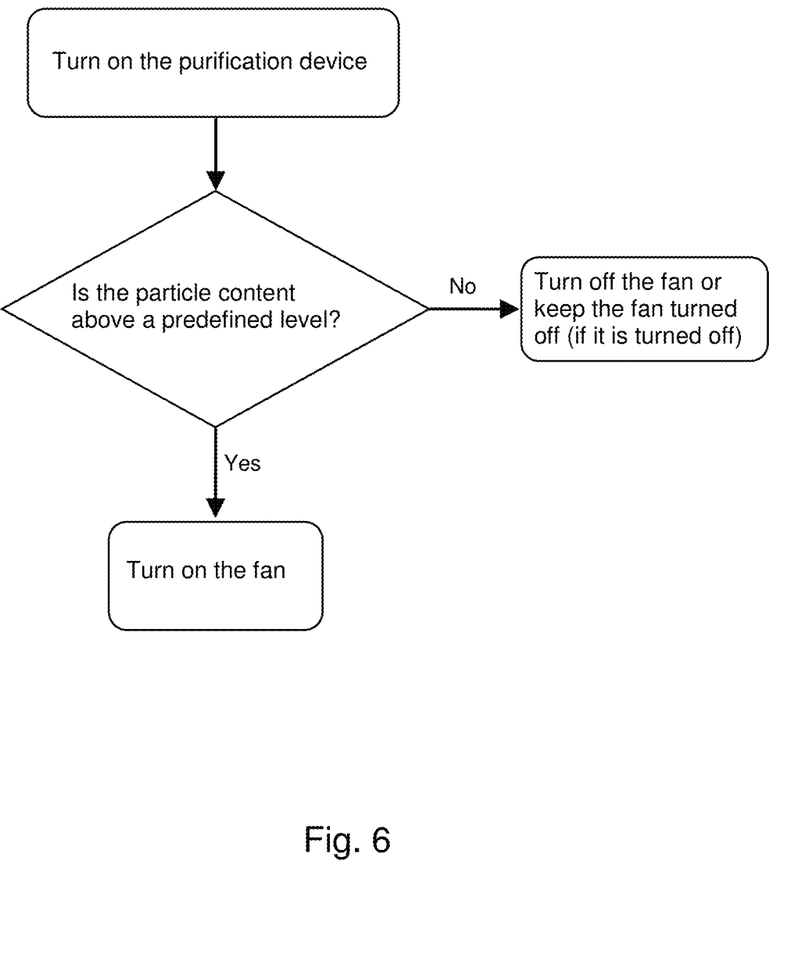
FIG. 6 shows a flow chart illustrating how the purification device according to the invention can be autonomously controlled by means of a particle sensor.

FIG. 4 illustrates a blown-up cross-sectional view of a portion of the inner space surrounded by a filter 20 of a purification device according to the invention. It can be seen that the filter 20 comprises a through-going opening 38 configured to retain large sized virus particles inside the inner space and allow small sized particle to pass through the filter 20 through the through-going opening 38.

A large number of virus particles 36 are placed near the entry to the through-going opening 38. The virus particles 36 are interconnected and arranged in a cloud-formed formation 34 comprising virus particles 36 and airway mucus. Accordingly, the cloud-formed formation 34 cannot escape through the through-going opening 38 even though the size of the individual virus particles 36 is smaller than the width D of the through-going opening 38. In fact, the cloud-formed formation 34 comprising virus particles 36 and airway mucus will stick to the inside surface of the filter 20.

The virus particles 36 are irradiated with UV light from a UV lamp (e.g. a UV C lamp) arranged to irradiate the air and particles present in the inner space. Since the virus particles 36 are trapped inside the space defined by the inner surface of the filter 20, there is sufficient time available to destroy the virus particles 36 by the ultraviolet (UV) light 50.

FIG. 5 illustrates a cross-sectional view of the bottom portion of a purification device 2 according to the invention. The purification device 2 comprises a housing 10 provided with a plurality of air outlet perforations 8' for allowing purified air 6 to leave the purification device 2.

The purification device 2 is configured to blow intake air 4 downwards into the inner space of the bottom portion of the purification device 2. Since the intake air 4 enters the purification device 2 in the top portion of the purification device 2, the intake air 4 will typically not suck particles from floor level into the purification device 2. The purified air 6 leaves the purification device 2 in a lower level than the level at which intake air 4 enters the purification device 2.

The purification device 2 comprises a UV light source (e.g. a UV C lamp) 14 configured to irradiate the intake air 4 flowing into the inner space 22 of the bottom portion of the purification device 2. Hereby, it is possible to disinfect the intake air inside the inner space 22 of the bottom portion of the purification device 2.

The purification device 2 comprises a HEPA filter 20 having a large number of pleats (as explained with reference to FIG. 3B) in order to achieve a small angle α (e.g. of 15 degrees or less as shown in and explained with reference to FIG. 3B) and a large total filter area.

The lowest position of the UV lamp 14 is the distal portion of the UV lamp 14 which is provided at a distance above the bottom plate 46 of the housing 10. Accordingly, an air gap 44 is provided between the bottom plate 46 of the housing 10 and the distal portion of the UV lamp 14. Wheels are rotatably attached to the bottom plate 46.

An additional layer 40 may optionally be arranged at the outside of the filter 20. In one embodiment, the additional layer 40 may be a layer that comprises activated carbon. Activated carbon can remove unwanted odors by acting as an adsorbent which will trap the odor inside the activated carbon and retain it.

An additional layer 40 may furthermore prevent UV light 50 from escaping to the surroundings.

In an embodiment, the additional layer 40 is an additional layer 40 sandwiched between the housing 10 and the filter 20, wherein the additional layer 40 comprises activated carbon.

FIG. 6 is a flow chart illustrating how the purification device according to the invention can be autonomously controlled by means of a particle sensor.

Initially the purification device is turned on. In one embodiment, the particle sensor of the purification device is turned on as default. In one embodiment, the particle sensor of the purification device is turned on and cannot be turned off.

The particle sensor of the purification device is configured to measure the particle content of the intake air. If the particle content of the intake air exceeds a predefined level, the fan of the purification device is turned on (or kept turned on if the fan has already been turned on).

If, on the other hand, the particle content of the intake air does not exceed the predefined level, the fan of the purification device is turned off (or kept turned off if the fan has already been turned off).

In one embodiment, both the fan and the UV lamp are turned on if the particle content of the intake air exceeds a predefined level.

In one embodiment, the speed of the fan is selected depending on the detected level of particle content.

In one embodiment, the speed of the fan can be set to two or more predefined non-zero levels.

In one embodiment, the speed of the fan can be set to three or more predefined non-zero levels.

In one embodiment, the speed of the fan can be gradually or non-gradually adjusted on the basis of the detected level of particle content. This may be done by fitting the fan with a permanent magnet motor and a frequency converter. This will furthermore allow the provision of the lowest possible energy consumption.

In one embodiment, the predefined particle content level is a default quantity. In another embodiment, however, the predefined particle content level can be adjusted by using a control unit of the purification device.

LIST OF REFERENCE NUMERALS

2 Purification device
4 Intake air
6 Purified air
8 Air inlet perforation
8' Air outlet perforation
10 Housing
12 Fan
14 Ultraviolet radiation lamp
16 Bottom portion
18 Top portion
20 Filter
22 Inner space (enclosure)
24 Wheel
26 Coarse filters
28 Control panel
30 Electrical plug
32 Pleat
34 Cloud-formed formation
36 Virus particle
38 Through-going opening
40 Additional layer
42 Air flow direction
44 Air gap
46 Bottom plate
50 Ultraviolet (UV) light
α, β, θ, ω Angle
D Width

The invention claimed is:

1. A purification device for disinfecting and filtering intake air, the purification device comprising:
- a housing provided with a number of inlet perforations for allowing the intake air to enter the housing and a number of air outlet perforations for allowing air purified by the purification device to leave the housing;
- a fan arranged inside the housing to suck the intake air into the housing and blow the purified air out of the housing;
- an ultraviolet radiation lamp arranged inside the housing to irradiate the intake air; and
- a high-efficiency particulate air (HEPA) filter surrounding the ultraviolet radiation lamp and arranged to filter the intake air before the intake air leaves the housing as purified air,
- wherein the filter is downstream of the fan relative to a direction of air flow through the purification device, and
- wherein the filter comprises a plurality of pleats arranged in such a manner that the angle between adjacent pleats is 30 degrees or less.

2. The purification device according to claim 1, wherein an air gap is provided between a bottom plate of the housing and a distal portion of the UV lamp.

3. The purification device according to claim 1, wherein the housing comprises a bottom portion and a top portion configured to be detachably attached to the bottom portion.

4. The purification device according to claim 3, wherein the fan is arranged in the top portion and a light irradiation portion of the UV lamp is arranged in the bottom portion.

5. The purification device according to claim 3, wherein the inlet perforations are provided in the top portion, whereas the outlet perforations are provided in the bottom portion.

6. The purification device according to claim 3, wherein the fan is positioned within the top portion, has a rotational axis oriented horizontal to a bottom plate of the housing, and has an outlet oriented perpendicular to the rotational axis.

7. The purification device according to claim 1, wherein the fan has a horizontally orientated intake portion and a vertical output portion so that air pressurised by the fan leaves the fan in a downwardly vertical direction.

8. The purification device according claim 1, wherein an additional layer is sandwiched between the housing and the filter, wherein the additional layer comprises activated carbon.

9. The purification device according to claim 3, wherein the top portion comprises a coarse filter slidably arranged in one or more filter tracks extending axially near a rim of the top portion.

10. The purification device according to claim 1, wherein the purification device comprises a particle sensor arranged to detect the level of particles in the air.

11. The purification device according to claim 1, wherein the purification device comprises a smoke alarm.

12. The purification device according to claim 10, wherein the purification device comprises a control unit configured to control the speed of the fan in dependence of the detected level of particles in the air.

13. A method for disinfecting and filtering intake air, wherein the method comprises the following steps:
- sucking intake air into a housing using a fan arranged inside the housing, wherein the intake air enters the housing through a number of inlet perforations provided in the housing;
- using the fan to blow purified air out from the housing through a number of air outlet perforations provided in the housing;
- irradiating the intake air using an ultraviolet radiation lamp arranged inside the housing; and
- filtering the intake air using a HEPA filter surrounding the ultraviolet radiation lamp before the intake air leaves the housing as purified air,
- wherein the filter is downstream of the fan relative to a direction of air flow through the purification device, and
- wherein the filter comprises a plurality of pleats arranged in such a manner that the angle between adjacent pleats is 30 degrees or less.

14. The method according to claim 13, wherein the irradiation is carried out by a UV lamp and an air gap is provided between a bottom plate of the housing and a distal portion of the UV lamp.

15. The method according to claim 13, wherein the housing comprises a bottom portion and a top portion configured to be detachably attached to the bottom portion.

16. The method according to claim 15, wherein the fan is arranged in the top portion and a light irradiation portion of the UV lamp is arranged in the bottom portion.

17. The method according to claim 16, wherein the inlet perforations are provided in the top portion, whereas the outlet perforations are provided in the bottom portion.

18. The method according to claim 13, wherein the fan has a horizontally orientated intake portion and a vertical output portion so that air pressurised by the fan leaves the fan in a downwardly vertical direction.

19. The method according to claim 13, wherein an additional layer is sandwiched between the housing and the filter, wherein the additional layer comprises activated carbon.

20. The method according to claim 13, further comprising a step of applying a coarse filter to filter the intake air before the intake air is sucked into the fan.

21. The method according to claim 13, further comprising a step of applying a particle sensor arranged to detect the level of particles in the air.

22. The method according to claim 13, further comprising a step of applying a smoke alarm to detect the smoke content in the air.

23. The method according to claim 21, further comprising a step of controlling the speed of the fan in dependence of the detected level of particles in the air.

24. The method according to claim 16, wherein the fan is positioned within the top portion, has a rotational axis oriented horizontal to a bottom plate of the housing, and has an outlet oriented perpendicular to the rotational axis.

* * * * *